US008092498B2

(12) United States Patent
Samudrala et al.

(10) Patent No.: US 8,092,498 B2
(45) Date of Patent: Jan. 10, 2012

(54) OCCIPITAL FIXATION SCREW

(75) Inventors: Srinath Samudrala, Pasadena, CA (US); Thomas Purcell, Del Mar, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 742 days.

(21) Appl. No.: 12/217,685

(22) Filed: Jul. 8, 2008

(65) Prior Publication Data

US 2009/0030463 A1 Jan. 29, 2009

Related U.S. Application Data

(60) Provisional application No. 60/958,883, filed on Jul. 9, 2007.

(51) Int. Cl.
*A61B 17/70* (2006.01)
*A61B 17/04* (2006.01)

(52) U.S. Cl. ......................... 606/250; 606/278; 606/264

(58) Field of Classification Search .................. 606/250, 606/254, 302, 279, 276, 278, 264, 301, 305, 606/272, 270, 268, 269
See application file for complete search history.

(56) References Cited

U.S. PATENT DOCUMENTS

| | | | | |
|---|---|---|---|---|
| 6,077,262 | A * | 6/2000 | Schlapfer et al. | 606/305 |
| 6,375,656 | B1 | 4/2002 | Faure | |
| 6,475,218 | B2 * | 11/2002 | Gournay et al. | 606/272 |
| 6,740,089 | B2 * | 5/2004 | Haider | 606/302 |
| 7,291,151 | B2 * | 11/2007 | Alvarez | 606/305 |
| 2003/0130659 | A1 | 7/2003 | Haider | |
| 2005/0080417 | A1 | 4/2005 | Alexis et al. | |
| 2006/0293664 | A1 | 12/2006 | Schumacher | |
| 2007/0016189 | A1 * | 1/2007 | Lake et al. | 606/61 |

FOREIGN PATENT DOCUMENTS

| | | |
|---|---|---|
| JP | 09-313502 | 12/1997 |
| WO | WO 2007/005561 A2 | 1/2007 |

OTHER PUBLICATIONS

International Search Report for Application No. PCT/US2008/008375 dated of mailing Oct. 24, 2008.

* cited by examiner

*Primary Examiner* — Pedro Philogene
(74) *Attorney, Agent, or Firm* — Michael R. Shevlin

(57) ABSTRACT

A surgical implant assembly and a method for securing a fixation rod, where the assembly is capable of being secured to a bone structure are disclosed. The assembly includes at least two rigid structures configured to be secured to the bone structure. The structures include a distal portion for receiving a portion of the fixation rod therebetween, a tab positioned at a distal point of the distal portion, a screw compression nut and a distal expansion member coupled to the screw compression nut that are driven down the rigid structures, and a rod compression nut and a proximal expansion member coupled to the rod compression nut that engage the rigid structures so that the fixation rod is disposed between the combination the screw compression nut and the distal expansion member and the combination of the rod compression nut and the proximal expansion member.

23 Claims, 8 Drawing Sheets

422
418
100
420
424
408
406

OCCIPITAL FIXATION SCREW

CROSS-REFERENCE TO RELATED APPLICATIONS

The present application claims priority to U.S. Provisional Patent Application No. 60/958,883, to Samudrala et al., filed Jul. 9, 2007, and entitled "Occipital Fixation Screw", and incorporates its disclosure herein by reference in its entirety.

BACKGROUND OF THE INVENTION

1. Field of the Invention

The present invention is generally directed and a bone anchor used for occipito-cervical fusion, more specifically, to an occipital fixation screw used as a bone anchor provided with tabs to increase surface and contact area to a bone structure.

2. Background

The spine is routinely subject to high loads which cycle during movement, whereby one of the primary concerns of physicians performing spinal implantation surgeries is the risk of screw pull-out. Screw pull-out occurs when the cylindrical portion of the bone which surrounds the inserted screw fails. A bone screw which is implanted perpendicular to the plate is particularly weak because the region of the bone which fails for pull-out to occur is only as large as the outer diameter of the screw. The amount of bone which must fail increases substantially as compared to pairs of screws which are implanted in parallel along the axis that the loading force is applied.

Along the spinal column, there are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate. Breaches of the esophageal wall permit bacterial contamination of the surrounding tissues, including the critical nerves in and around the spinal cord. Such contamination can be fatal.

Thus, it is desirable to provide improved systems for stabilizing the affixation of a bone plate to a bone structure.

SUMMARY OF THE INVENTION

Some embodiments of the present invention minimize, and in some aspects eliminate, the above-mentioned failures, and other problems, by utilizing the structural features described herein. Thus, the result is an improved system and method for stabilizing a fixation screw to a bone structure, such as the skull.

In some embodiments, the present invention relates to a surgical implant assembly for securing a fixation rod and capable of being secured to a bone structure. The assembly includes at least two rigid structures configured to be secured to the bone structure. Each structure includes a distal portion configured to receive a portion of the fixation rod therebetween and a tab positioned at a distal point of the distal portion and configured to outwardly extend away from an interior portion of the rigid structure. The assembly further includes a screw compression nut and a distal expansion member coupled to the screw compression nut. A combination of the screw compression nut and the distal expansion member is configured to be driven down the at least two rigid structures for positioning the combination adjacent the bone structure. The assembly also includes a rod compression nut and a proximal expansion member coupled to the rod compression nut. A combination of the rod compression nut and the proximal expansion member is configured to engage the two rigid structures so that the fixation rod is disposed between the combination of the screw compression nut and the distal expansion member and the combination of the rod compression nut and the proximal expansion member.

In some embodiments, the present invention relates to a method for securing a fixation rod to a bone structure. The method includes creating an opening within the bone structure, inserting at least two rigid structures into the opening in the bone structure. Each of the at least two rigid structures includes a distal portion configured to receive a portion of the fixation rod therebetween and a tab positioned at a distal point of the distal portion and configured to outwardly extend away from an interior portion of the rigid structure. The method further includes radially expanding the tabs within the opening in the bone structure, thereby engaging the bone structure, installing a screw compression nut and a distal expansion member coupled to the screw compression nut in the at least two rigid structures, positioning the screw compression nut and the distal expansion member adjacent to the opening in the bone structure, inserting the fixation rod between the at least two rigid structures and above a combination of the screw compression nut and the distal expansion member, wherein a portion of the fixation rod bears against top surfaces of the screw compression nut and the distal expansion member, and installing a rod compression nut and a proximal expansion member coupled to the rod compression nut in the at least two rigid structures above the fixation rod, wherein bottom surfaces of the rod compression nut and the proximal expansion member are configured to bear against the fixation rod.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the drawings, subsequent detailed description and appended claims.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION OF THE INVENTION

Figure 1:
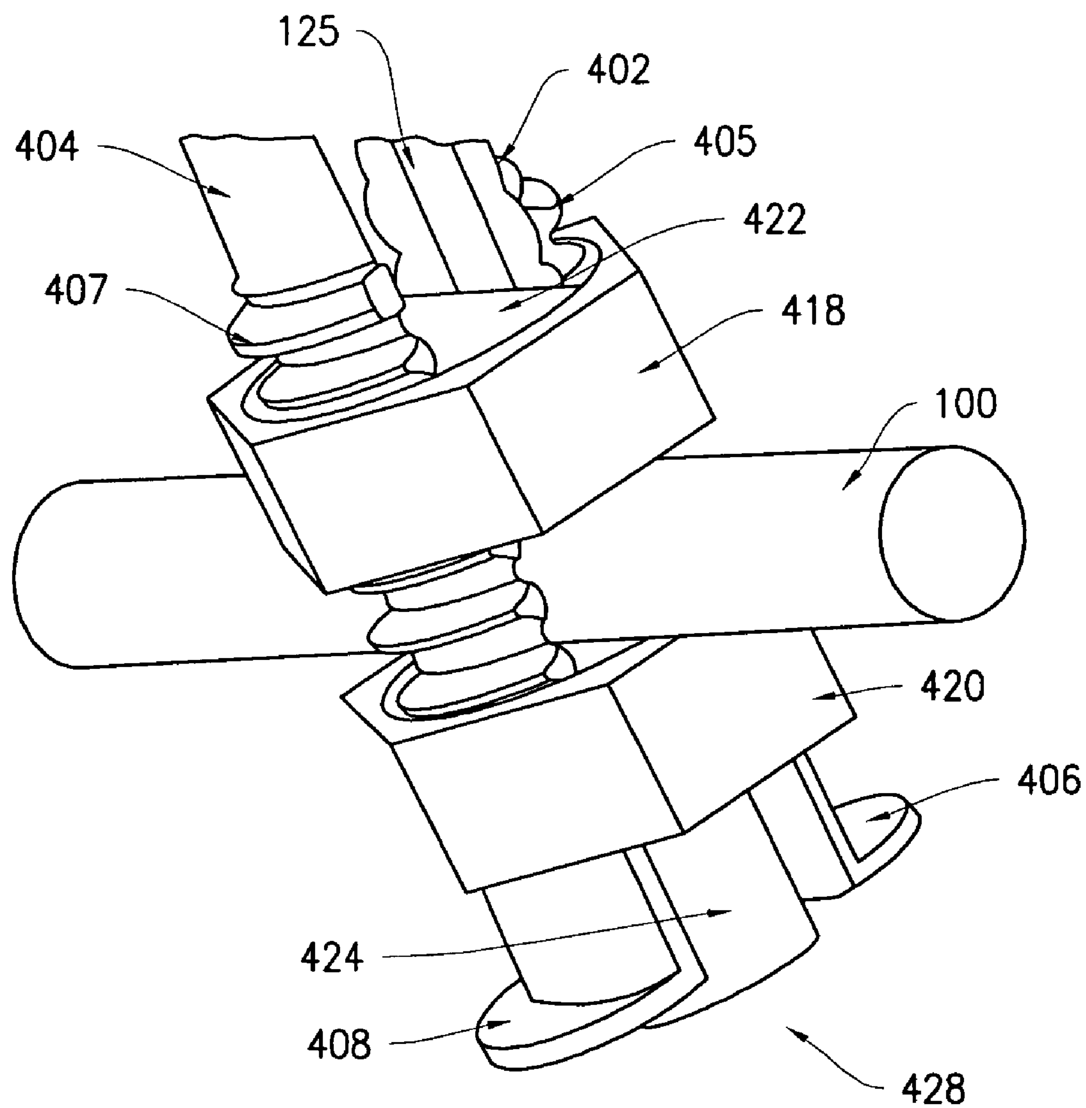
FIG. 1 is a perspective view of a portion of an exemplary occipital fixation screw, according to some embodiments of the present invention.

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. These and other embodiments are disclosed or are apparent from and encompassed by, the following description.

In this respect, before a description of the embodiments of the invention in detail, it is to be understood that the invention is not limited in its application to the details of construction and to the arrangements of the components set forth in the following description or illustrated in the drawings. The invention is capable of other embodiments and of being practiced and carried out in various ways where particular configurations, process steps, and materials disclosed herein as such configurations, process steps, and materials may vary somewhat. In addition, it is to be understood that the phraseology and terminology employed herein are for the purpose of the description and should not be regarded as limiting. Furthermore, as will be apparent to those skilled in the art, the present invention may be embodied in other specific forms without departing from the essential characteristics thereof.

For purposes of the description of the drawings and the embodiments of the present invention, as mentioned for each drawing, each figure may not drawn to scale. Some areas drawn may be bigger and/or simpler in order to clearly portray the improvement to what has already been established. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed. It is also to be understood that the terminology employed herein is used for the purpose of describing particular embodiments only and is not intended to be limiting since the scope of the present invention will be limited only by the appended claims and equivalents thereof.

Some embodiments of the present invention relate to a spinal implant assembly comprising an occipital fixation screw used as a bone anchor for occipito-cervical fusion. In an embodiment of the present invention, the bone anchor device used for occipito-cervical fusion provides significant strength to a screw implantation, and more specifically, to a thin bone structure due to the tabs at the distal end of the device. The tabs are placed through a hold in the occiput (the back part of the head or skull), and then expanded radially. The tabs have an increased surface and contact area that allows them to resist pullout forces.

FIGS. 1-11 illustrate exemplary embodiments of a spinal implant assembly having an occipital fixation screw used as a bone anchor and including a fixation rod, screw tangs (e.g., elongated, rigid structures), a temporary screw cap, a distal expansion member, a proximal expansion member and compression nuts (rod and screw).

Figure 4:
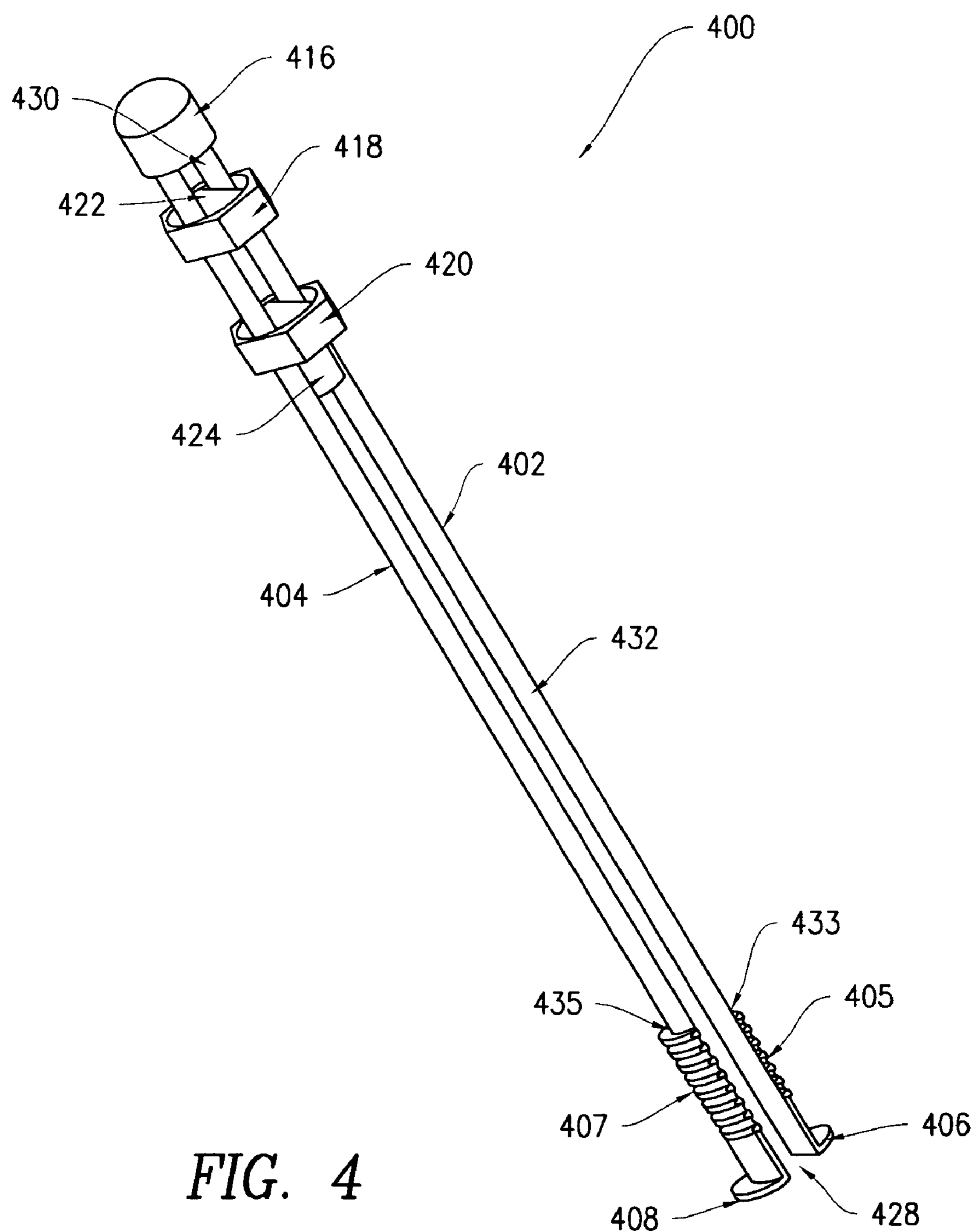
FIG. 4 is a perspective view of an entire occipital fixation screw assembly, according to some embodiments of the present invention.

Referring to FIG. 4, a perspective view of an exemplary spinal implant assembly 400 is illustrated. Spinal assembly 400 includes screw tangs 402 and 404, a screw compression nut 420, a rod compression nut 418, a proximal expansion member 422, and a distal expansion member 424, and a temporary screw cap 416. The tangs 402 and 404 both include a proximal portion 430, a distal portion 428, and a middle portion (or a tower portion) 432 disposed between the proximal portion 430 and a distal portion (or breakaway portion) 428. The tangs 402, 404 further include tab portions 406, 408, respectively, that are disposed at the distal portion 428 of the tangs. The tab portions 406, 408 are configured to protrude outwardly and away from each other from the distal portion 428 of each tang 402, 404. In some embodiments, the tab portions 406, 408 are configured to be substantially perpendicular to the body portions of the tangs 402, 404. In some embodiments, the tab portions can protrude at any desired angles. The tab portions are configured to secure the tangs 402, 404 to the bony matter (such as to a hole in a skull). The distal portions of each tang 402, 404 also include threaded portions 405, 407, respectively. The threaded portions 405, 407 are configured to accommodate placement of the compression nuts 418 and 420. In some embodiments, the threaded portions 405, 407 are configured to extend throughout the entire body portions of the tangs 402, 404.

In some embodiments, the shape of each tang 402, 404 can be configured to be partially circular so as to accommodate placement of the compression nuts 402, 404 as well as placement of the members 422 and 424 between the tangs 402, 404.

In some embodiments, the tangs 402, 404 can be secured together using the temporary screw cap 416. The screw cap 416 can be secured at the proximal portion 430 of each tang 402, 404. The screw cap 416 can include a threaded portion disposed on its interior portion, where the screw cap's threaded portion corresponds to the threads on the tangs 402, 404 that are disposed at the proximal portion of the tangs. In some embodiments, the screw cap 416 can be simply friction-fit on top of the tangs at the proximal portion 430. In some embodiments, the entire tang body can be threaded, or in the alternative, any array of combinations of body parts of the tangs can be threaded.

In some embodiments, the tangs 402, 404 include breakaway portions 433, 435, respectively. The breakaway portions 433, 435 are configured to be disposed above the threaded portions 405, 407 on each tang 402, 404, respectively. The breakaway portions 433, 435 are configured to allow a surgeon (or any other medical professional) to remove unused portions of the tangs 402, 404 after implantation of the tangs and a fixation rod into a bony matter. In some embodiments, the breakaway portions 433, 435 are configured to be depressions in the body of the tangs 402, 404 that allow a surgeon (or other medical professional) to bend and break the tangs. As can be understood by one skilled in the art, the breakaway portions 433, 435 can be disposed anywhere on the bodies of the tangs 402, 404, respectively. As can be further understood by one skilled in the art, there are other embodiments of the breakaway portions 433, 435. The breakaway portions 433, 435 can be configured to be a breakable web of material that allows the tower sections of the tangs 402, 404 to be easily removed (e.g., the web of materials are broken). The breakaway portions can be included at the transition of the tower portion and the base of each tang.

In some embodiments, the tab portions 406, 408 can be placed through a hole in the occiput. As stated above, the tab portions are configured to protrude from the proximal ends of each tang 402, 404 at the 90° angle (although other angles may be used) outward. To install the assembly 400 into a bony matter, the tangs 402, 404 are compressed or squeezed together for implantation into a hole, which is previously created in the bone. In some embodiments, the size of the hole can be approximately equal to the size (e.g., diameter) of the circle that is created by the tangs in an uncompressed state. Further, in order to secure the tangs 402, 404 inside the hole, the size of the hole is less than the distance between outermost points of each tab portion in when the tangs are in their uncompressed state. After inserting the tangs into the hole, the tangs 402, 404 are configured to expand in a radial direction, thus, allowing the tabs 406, 408 to engage the bone structure in the occiput.

Figure 2:
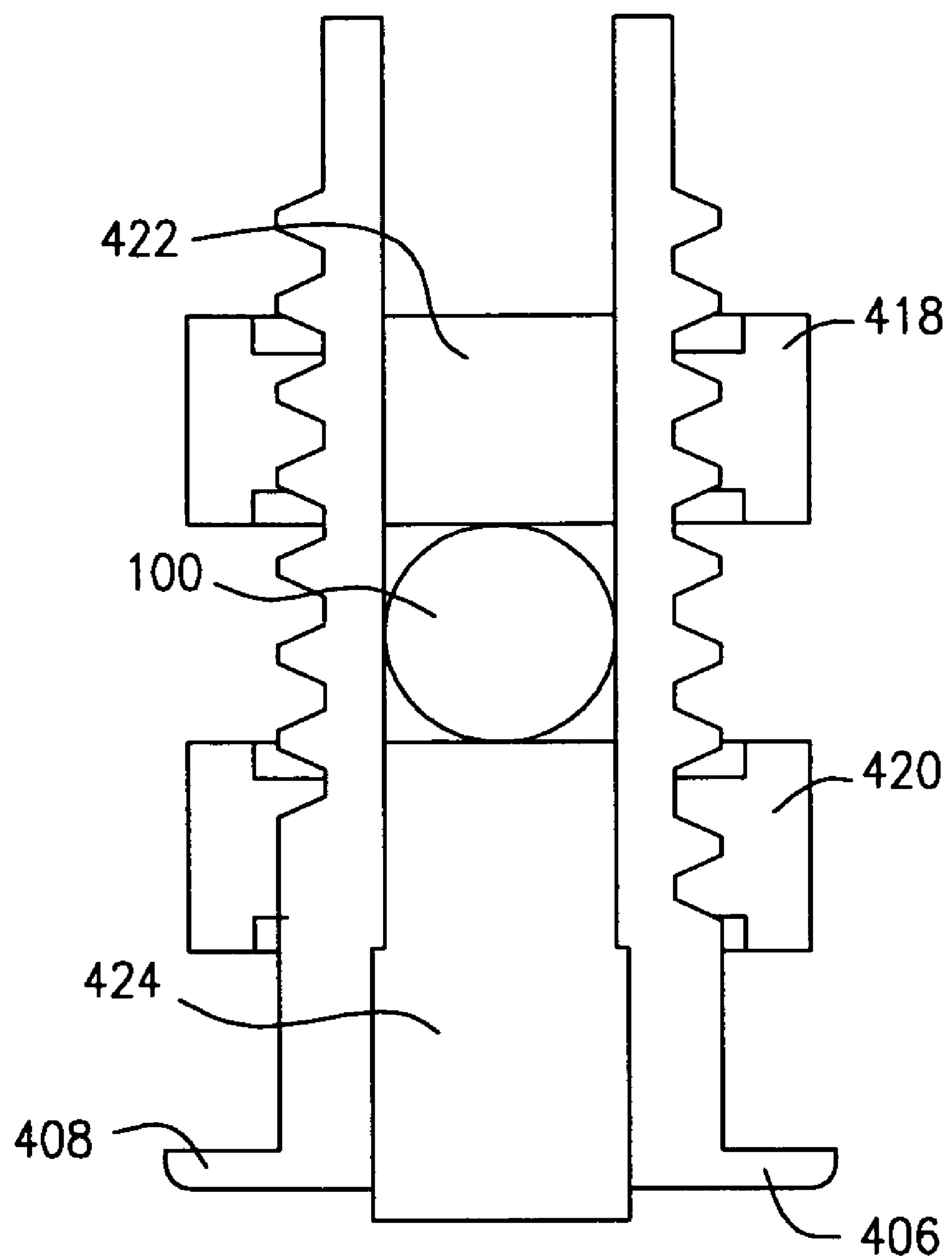
FIG. 2 is a side view of the portion of the occipital fixation screw shown in FIG. 1.
Figure 3:
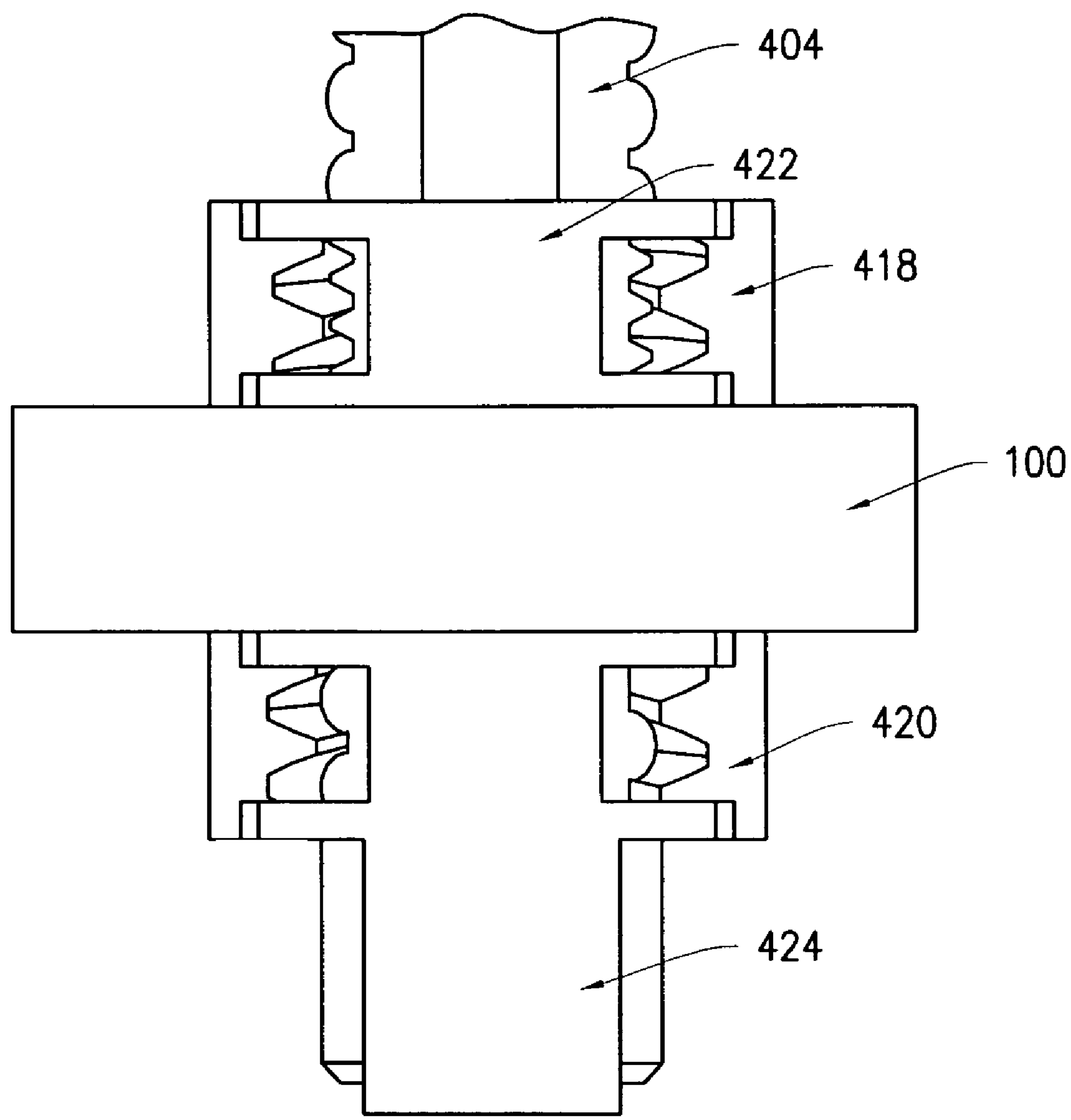
FIG. 3 is another side view of the portion of the occipital fixation screw shown in FIG. 1.

As stated above, the assembly 400 further includes the screw compression nut 420 and the rod compression nut 418 that are driven toward the distal portion 428 along with respective the distal expansion member 424 and the proximal expansion member 422. FIGS. 1-3 are a perspective view and side views of a portion of the assembly 400 showing securing of a fixation rod 100 using the compression nuts 418, 420 and the expansion members 422, 424. As shown in FIGS. 1-3, the fixation rod 100 is configured to be secured between the screw compression nut 420 along with the distal expansion member 424 and the rod compression nut 418 along with the proximal expansion member 422. The rod 100 is configured to be secured near the distal portion 428 of the tangs 402, 404. The expansion members 422, 424 are configured to be secured between the tangs' interior portions 125 and the compression nuts 418, 420, respectively. In some embodiments, the interior portions 125 of the tangs 402, 404 are configured to include a rounded cavity, wherein the shape of the expansion members 422, 424 is configured to match the rounded cavity, thus, allowing smooth sliding/driving down along the interior portions 125 of the tangs 402, 404. The expansion members 422, 424 can further include threaded portions (not shown in FIGS. 1-4) that can match the interior threads of the compression nuts 418, 420, so that, during rotation of the nuts 418, 420, the expansion members are configured slide along the interior portions 125 of the tangs 402, 404 without rotating with the compression nuts 418, 420. In some embodiments, the expansion members 422, 424 can be configured to slide down the interior portions 125 of the tangs 402, 404 without being secured to the compression nuts 418, 420.

In some embodiments, the expansion member 422 is configured have the same thickness as the thickness of the rod compression nut 418. The compression nut 418 is configured to be flush against the expansion member 422 thereby creating smooth top and bottom surfaces (where the bottom surface is configured to interact with the fixation rod 100, as show in FIGS. 1-3). In some embodiments, the expansion member 424 can be configured to have a greater thickness than the thickness of the screw compression nut 420. The top surface of the expansion member 424 can be configured to be flush with the compression nut 420, thus, creating a smooth surface with the compression nut 420. The bottom portion of the expansion member 424 is configured to extend toward the tab portions 406, 408 and to be flush against the bottom portions of the tab portions 406, 408. In some embodiments, the bottom portion of the expansion member 424 can extend beyond the tab portions 406, 408 and into the hole created in the bony matter. In some embodiments, the compression nuts 418, 420 and the respective expansion members 422, 424 can be separately installed into the assembly 400. For example, the compression nut 418 can be screwed onto the portions 405, 407 and then the expansion member 424 can be placed into the interior portion 125 of the tangs 402, 404 and slid down into the compression nut 420. The expansion member 422 can be installed similarly. In some embodiments, the expansion members 422, 424 can be installed first, followed by the installation of the compression nuts 418, 420, respectively. Further, a locking mechanism can be used to secure the compression nuts to the expansion members. An exemplary installation procedure of the assembly 400 into the bony matter is discussed below in connection with FIGS. 5-11.

The rod 100 is secured between the bottom portion of the expansion member 422 and the top portion of the expansion member 424. The bottom and top portions of the respective members 422, 424 can have smooth surfaces or, in the alternative, can have curved surfaces configured to accommodate placement of the rod 100. The curved surfaces can have a matching curvature to the curvature of the rod 100, thereby further securing the rod 100 between the members 422, 424.

Referring back to FIG. 4, in some embodiments, the tangs 402, 404 can be expanded using an additional force created by advancing the distal expansion member 424 and proximal expansion member down between the bodies of the tangs. Since, the tabs 406, 408 have an increased surface area and contact area that engages the bone structure outside of the hole of the occiput, the implant assembly 400 resists pullout forces.

In some embodiments, the tangs 402, 404 can be separately inserted into two separate openings made in the bony matter. To install the tangs 402, 404, the respective tabs 406, 408 are initially inserted into the bony matter and then the tangs 402, 404 are rotated toward each other so that the tangs 402, 404 are substantially parallel to each other, thereby allowing installation of the compression nuts 418, 420, and the expansion members 422, 424. This procedure advantageous as it does require drilling of a larger opening in the bony matter and further allows the expansion member 424 to be flush against the un-drilled portion bone, thereby creating a more secure installation of the assembly 400 into the bony matter.

Figure 5:
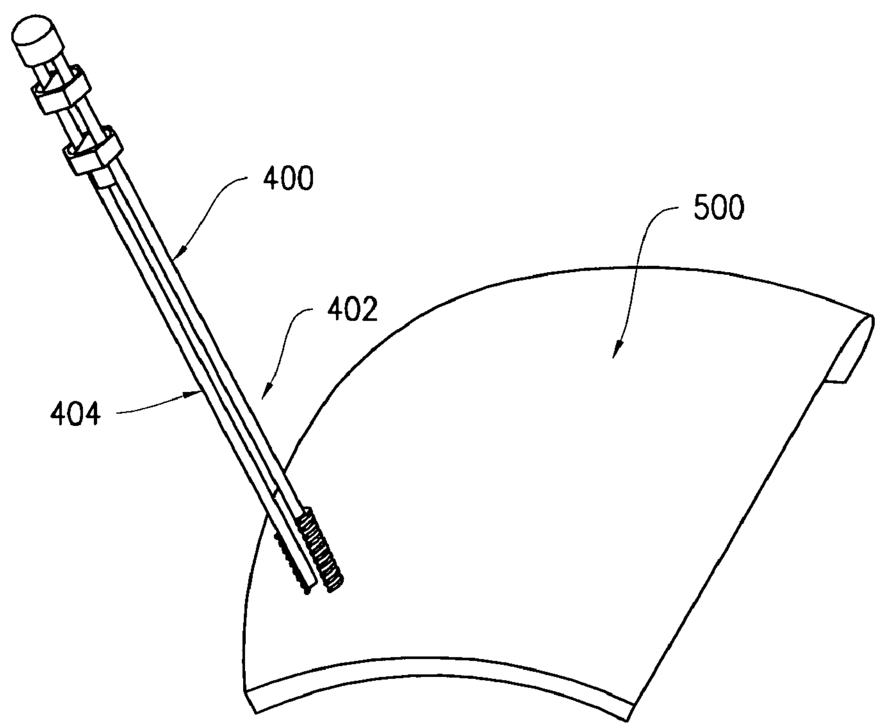
FIGS. 5-11 are perspective view of an exemplary implementation of the occipital fixation screw assembly into a bone matter, according to some embodiments of the present invention.
Figure 6:
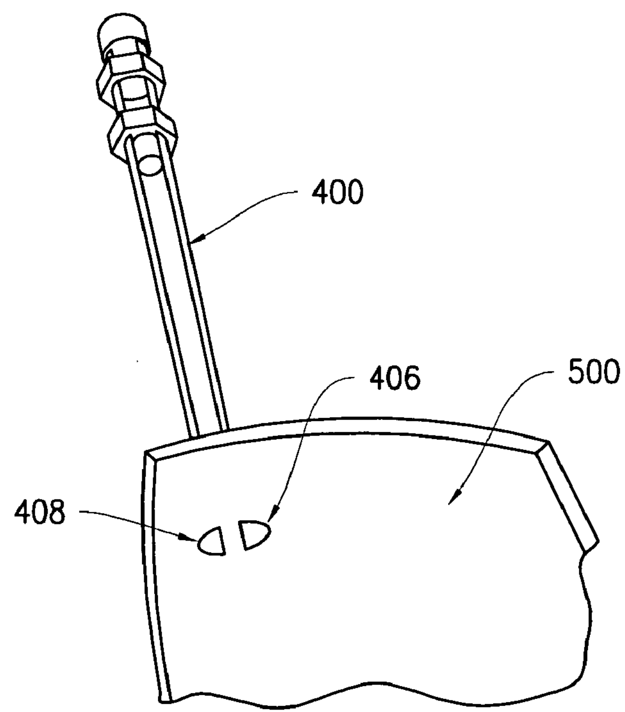
Figure 7:
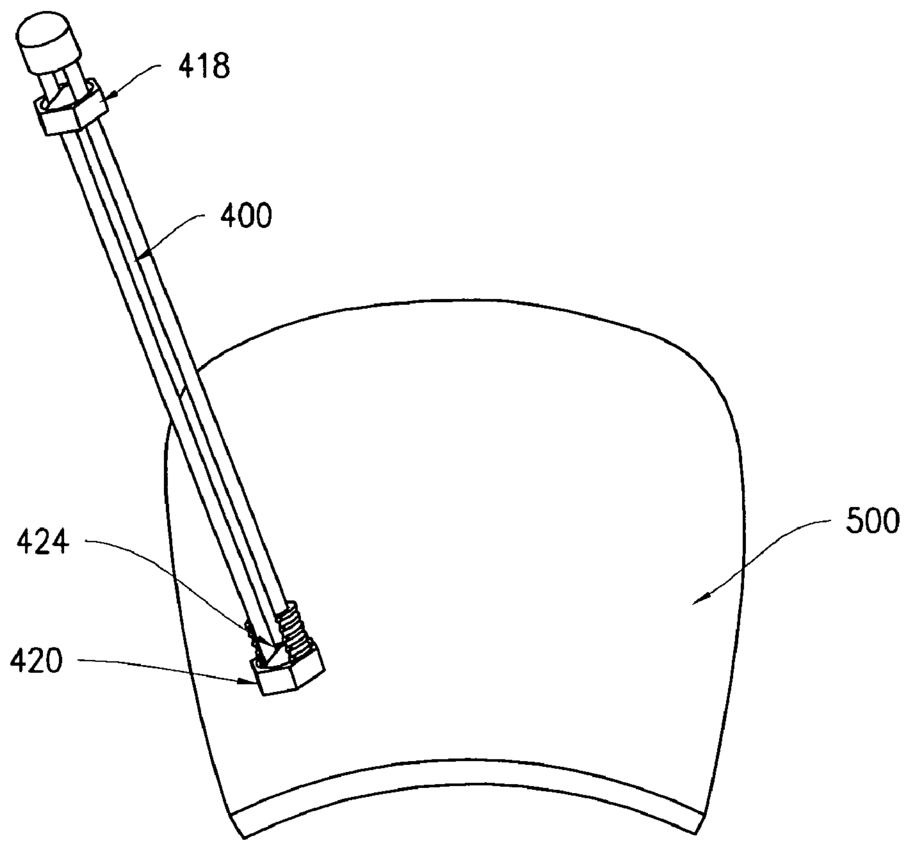

Referring to FIGS. 5-7, once the tangs are inserted into the hole in the occiput (FIG. 5) and the tabs engage the inside surface area of the bone structure 500 (FIG. 6), a screw compression nut 420 is placed over the parallel tangs 402, 404 and affixed to the tangs adjacent to the hole (FIG. 7). As stated above, the tangs 402, 404 include threaded exterior surfaces 405, 407, respectively, which engage at least one nut or fastening screw. In some embodiments, the tangs 402, 404 are threaded in the distal portion 428 (as shown in FIGS. 1-11). Accordingly, the screw compression nut 420 is driven down the body of the tangs 402, 404, where it is inserted into place adjacent the hole in the bone structure and then affixed to the tangs 402, 404 using torque, i.e., the compression nut 420 is screwed along the threaded portions 405, 407, respectively toward the bone structure. Along with the screw compression nut 420, the distal expansion member 424 is also installed. The expansion member 424 is installed between the tangs 402, 404. In some embodiments, the screw compression nut 420 and distal expansion member 424 are driven down the tangs 402, 404 in direct correlation to one another. The installation process results in the top portion of the distal expansion member 424 being flush with the top portion of the screw compression nut 420, thereby creating a flush surface for reception of the fixation rod 100. Alternative embodiments may exist where surfaces of the distal expansion member and screw compression nut do not align.

Figure 8:
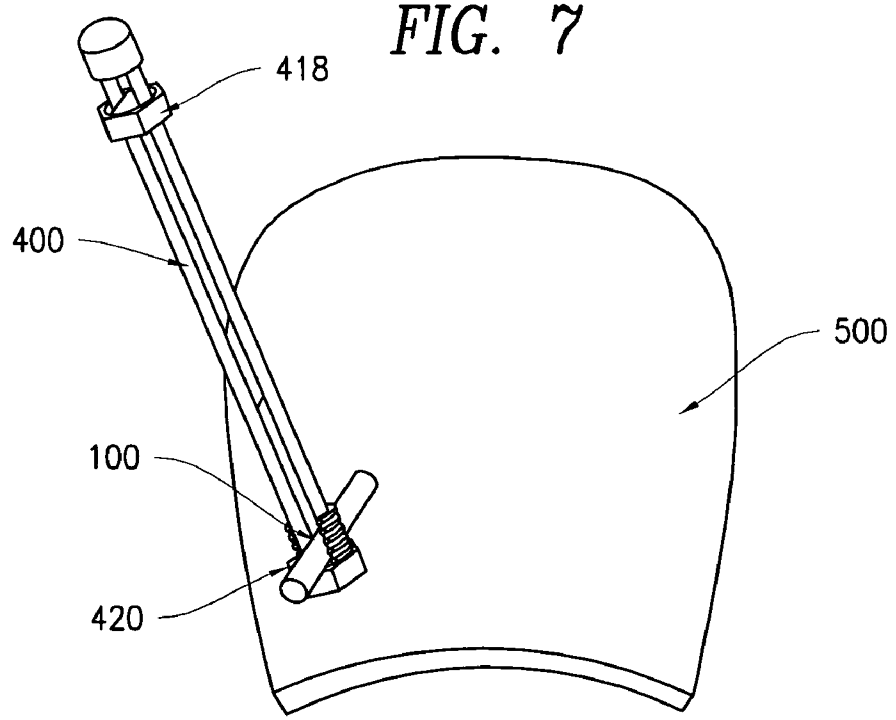
Figure 9:
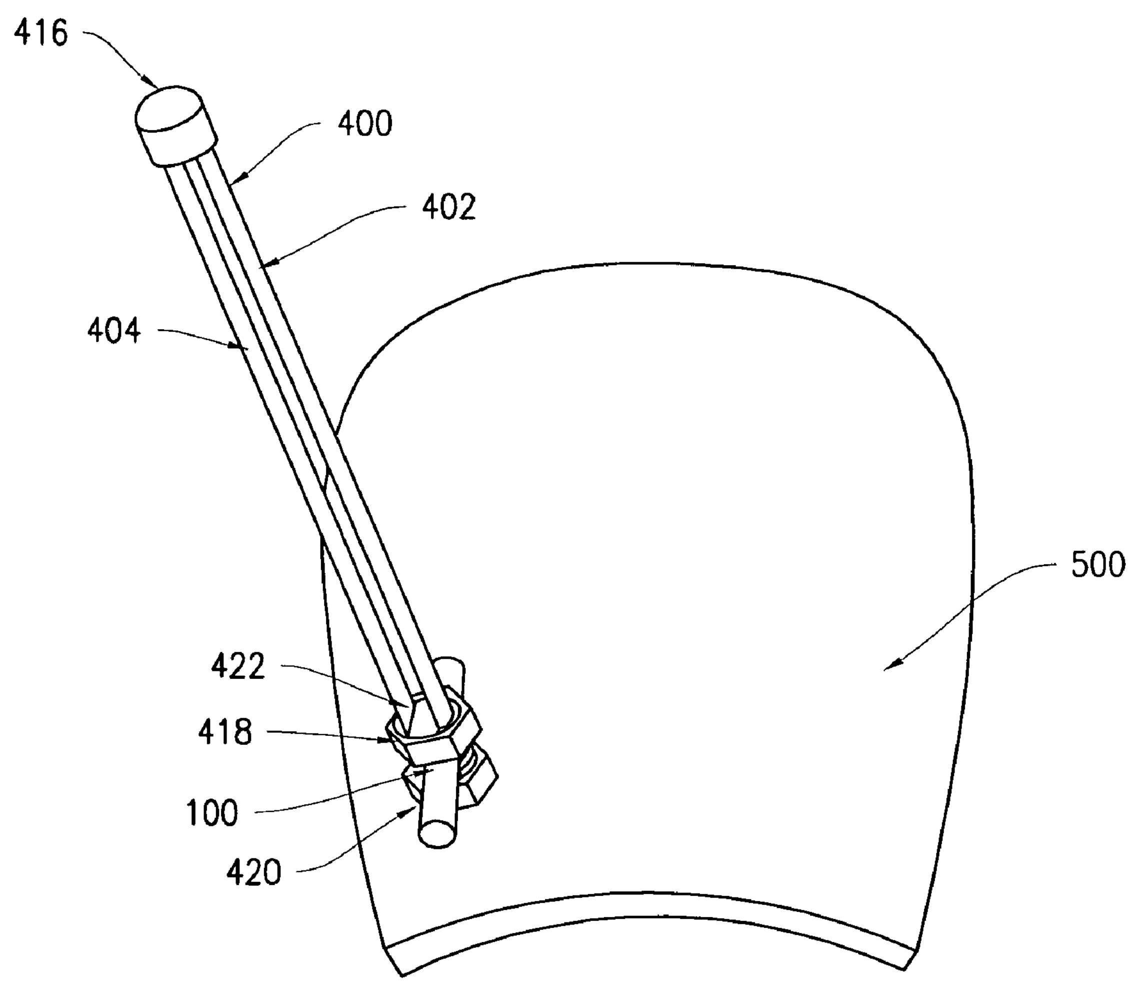

Referring to FIGS. 8-9, once the screw compression nut 420 is in place, the fixation rod 100 is inserted. The fixation rod 100 is positioned directly above the screw compression nut 420 and between the tangs 402, 404. The fixation rod 100 can be contoured to fit the locations between the tangs 402, 404 and can be saddled in any position or location. The fixation rod 100 provides strength and maintains the spinal implant assembly.

In direct correlation to the screw compression nut, the rod compression nut 418 us driven down the tangs 402, 404 and positioned adjacent the fixation rod 100. In some embodiments, the rod compression nut 418 is affixed to the proximal expansion member 422. In some embodiments, the rod compression nut 418 and proximal expansion member 422 are driven down to the tangs 402, 404 in direct correlation to one another. The top surface and bottom surface of the proximal expansion member 422 are configured to be flush with the respective top and bottom surfaces of the rod compression nut 418 (as shown in FIGS. 1-3), thus, creating a flush surface for bearing against the fixation rod 100 and a flush top surface. In some embodiments, the surfaces of the proximal expansion member 422 and rod compression nut 418 are configured to not align.

The rod compression nut 418 is also configured to be screwed along the threaded portions 405, 407 of the tangs 402, 404, respectively, in a direction toward to the bone structure 500. In some embodiments, the rotation of the compression nuts 418, 420 can be in clockwise or in counterclockwise directions to prevent disengagement or loosening of the rod 100 from the assembly 400. In some embodiments, the compression nuts 418, 420 and/or the threaded portions 405, 407 can include locking mechanism that lock the compression nuts 418, 420 in place to prevent rotational movement of the compression nuts 418, 420, and ultimate loosening of the rod 100.

After insertion of the rod between the compression nut 418 along with expansion member 422 and the compression nut 420 along with expansion member 424, the fixation rod 100 is positioned between the screw compression nut 420 and the rod compression nut 424, the rod compression nut 424 is configured to bear against a portion of the fixation rod 100, as shown in FIGS. 1-3 and 9. The rod 100 is then tightened (or further rotated toward the bone structure 500) to secure and maintain positioning of the fixation rod 100.

All during the implantation of the tangs 402, 404, engagement of the tabs 406, 408, insertion of the screw compression nut 420, fixation rod 100 and subsequent rod compression nut 418, the temporary screw cap 416 may be used to maintain a position atop the tangs, holding them in a relative position so that they can be compressed together, and the compression nuts 418, 420 can be driven down the middle portion 432 of the tangs 418, 420. In some embodiments, the temporary screw cap 416 includes the feature of affixing onto the tops of the screw caps via a threaded feature or that of a clipping attachment.

Figure 10:
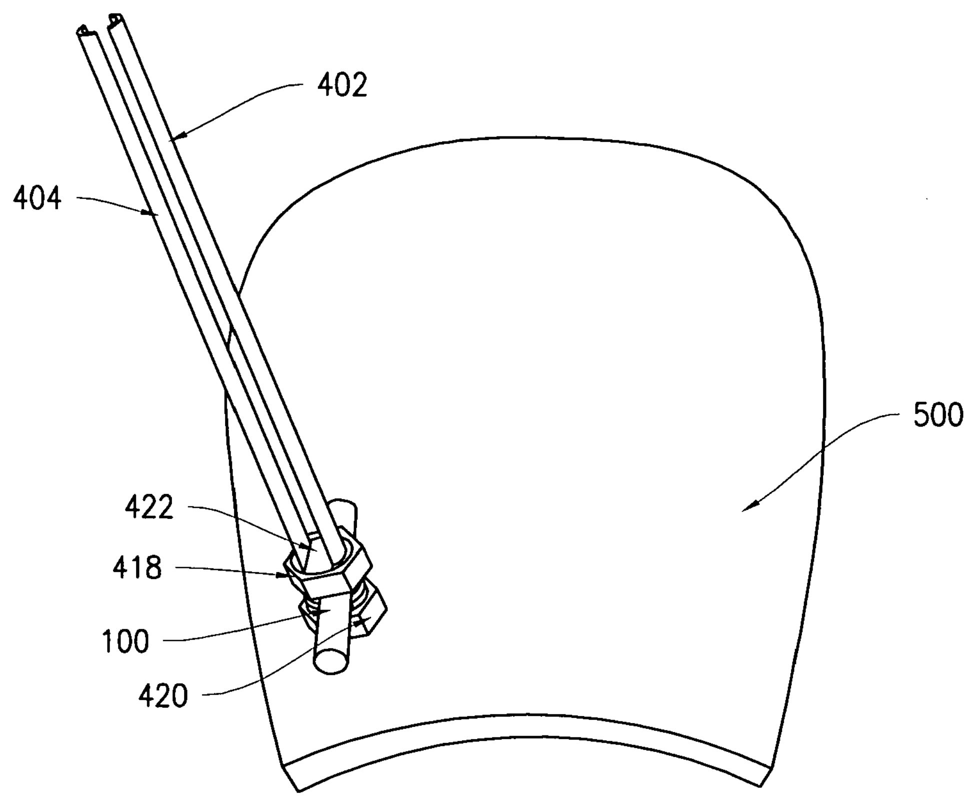

Referring to FIG. 10, once the rod compression nut 418 is set into place, the temporary screw cap 416 is removed. The removal of the cap 416 can be unscrewed from the threaded portions of the tangs 402, 404 disposed at the proximal portion of the tangs.

Figure 11:
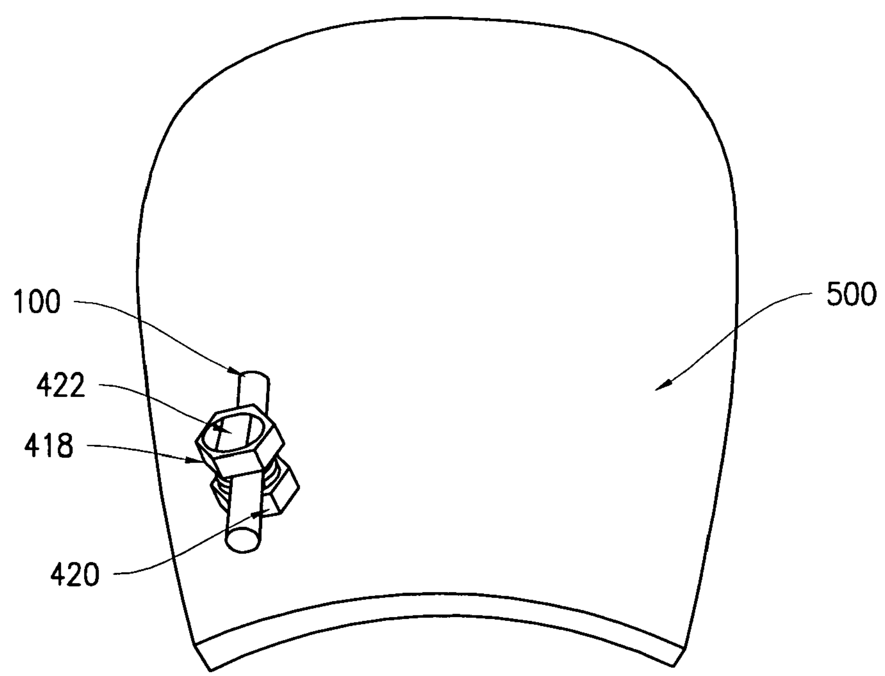

After all the components are in place and the temporary screw cap 416 is removed, the tower or middle portion 432 of each one of tangs 402, 404 is broken off or otherwise removed at the respective breakaway portions 433, 435, as shown in FIG. 11. Thus, a flush, smooth surface of the spinal implant assembly remains. The spinal implant assembly 400 can be fully implanted, and thus, provides for an improved stability and increased resistance to pullout.

As can be understood by one skilled in the art, the rod 100 can have various shapes and sizes and the compression nuts 418, 420 along with expansion members 422, 424 can be adjusted accordingly to accommodate insertion of a particular shape of the fixation rod 100. The compression nuts 418, 420 can be secured to the tangs 402, 404 via a threading arrangement, a snap-fit arrangement, a clip arrangement, or any other arrangement.

In some embodiments, the tangs 402, 404, the compression nuts 418, 420, the expansion members 422, 424 can be manufactured from the same or different materials, which can include titanium, or any other biocompatible materials.

In some embodiments, the compression nuts and respective expansion members can be unitary structures (i.e., a single structure for the combination of a compression nut and an expansion member). In some embodiments, the compression nuts and respective expansion members can be separate from each other.

As can be further understood by one skilled in the art, there can be any number of assemblies 400 installed in the bone structure 500. The assemblies 400 can implement any number of rods 100, which can be connected to one another. The assembly 400 can be configured to accommodate securing a plurality of rods 100 between the tangs 402, 404.

While illustrative embodiments of the invention have been described above, it is, of course, understood that various modifications will be apparent to those of ordinary skill in the art. Such modifications are within the spirit and scope of the invention, which is limited and defined only by the appended claims.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A surgical implant assembly for securing a fixation rod and capable of being secured to a bone structure, comprising:
- at least two separate rigid structures configured to be secured to the bone structure, each having:
  - a distal portion configured to receive a portion of the fixation rod therebetween;
  - an outwardly facing tab positioned at a distal point of the distal portion;
- a screw compression nut and a distal expansion member coupled to the screw compression nut, wherein a combination of the screw compression nut and the distal expansion member is configured to be driven down the at least two rigid structures and further configured to expand the distal portion of the at least two rigid structures and outwardly facing tabs apart; and
- a rod compression nut and a proximal expansion member coupled to the rod compression nut, wherein a combination of the rod compression nut and the proximal expansion member is configured to engage the two rigid structures so that the fixation rod is disposed between the combination of the screw compression nut and the distal expansion member and the combination of the rod compression nut and the proximal expansion member.

2. The assembly according to claim 1, wherein each of the at least two rigid structures includes a proximal portion and a middle portion disposed between the proximal portion and the distal portion.

3. The assembly according to claim 2, wherein the combination of the screw compression nut and the distal expansion member is configured to be driven down the middle portion of the at least two rigid structures toward the distal portion of the at least two rigid structures.

4. The assembly according to claim 3, wherein the combination of the rod compression nut and the proximal expansion member is configured to be driven down the middle portion of the at least two rigid structures toward the distal portion of the at least two rigid structures.

5. The assembly according to claim 2, wherein the middle portion and the distal portion of each of the at least two rigid structures are separated by a breakaway portion configured to allow removal of the middle portion from the distal portion upon securing of the fixation rod between the combination of the screw compression nut and the distal expansion member and the combination of the rod compression nut and the proximal expansion member.

6. The assembly according to claim 1, wherein the distal portion of each of the at least two rigid member is configured to be threaded, thereby allowing threaded engagement between the screw compression nut, the rod compression nut and each respective rigid member.

7. The assembly according to claim 1, wherein the tab of each of the at least two rigid structures is configured to be inserted into at least one opening created in the bone structure.

8. The assembly according to claim 7, wherein the tabs are configured to expand radially within the opening in the bone structure subsequent to being placed into the opening, thereby engaging the bone structure.

9. The assembly according to claim 8, wherein the tabs and the rigid structures are configured to be angularly disposed with respect to one another.

10. The assembly according to claim 9, wherein the tabs and the rigid structures are configured to be substantially perpendicular to each other.

11. The assembly according to claim 6, wherein the screw compression nut is configured to be driven down the middle portion via a threaded engagement with the threaded distal portion and the distal expansion member is configured to be driven between the at least two rigid structures.

12. The assembly according to claim 11, wherein the rod compression nut is configured to be driven down the middle portion via the threaded engagement with the threaded distal portion and the proximal expansion member is configured to be driven between the at least two rigid structures.

13. The assembly according to claim 2, further comprising a temporary screw cap configured to be affixed at the proximal portion of the at least two rigid structures and further configured to secure the at least two rigid structures in a substantially parallel arrangement, wherein the temporary screw cap is configured to be removed after the fixation rod is secured between the combination of the screw compression nut and the distal expansion member and the combination of the rod compression nut and the proximal expansion member.

14. The assembly according to claim 1, wherein each tab of the at least two rigid structures is inserted into a separate opening created in the bone structure.

15. The assembly according to claim 14, wherein upon installation between the respective distal portions of the at least two rigid structures, the distal expansion member is configured to be flush against the bone structure.

16. The assembly according to claim 1, wherein top surfaces of the screw compression nut and a distal expansion member and bottom surfaces of the rod compression nut and proximal expansion member are configured to be flush against the fixation rod upon installation of the rod between the combination of the screw compression nut and the distal expansion member and the combination of the rod compression nut and the proximal expansion member.

17. A method for securing a fixation rod to a bone structure, the method comprising the steps of:

creating an opening within the bone structure;

inserting at least two separate rigid structures into the opening in the bone structure, wherein each of the at least two rigid structures includes a distal portion configured to receive a portion of the fixation rod therebetween, and an outwardly facing tab positioned at a distal point of the distal portion;

radially expanding the outwardly facing tabs within the opening in the bone structure, thereby engaging the bone structure;

installing a screw compression nut and a distal expansion member coupled to the screw compression nut in the at least two rigid structures;

positioning the screw compression nut and the distal expansion member near the distal portion to expand the distal portion of the at least two rigid structures apart;

inserting the fixation rod between the at least two rigid structures and above a combination of the screw compression nut and the distal expansion member, wherein a portion of the fixation rod bears against top surfaces of the screw compression nut and the distal expansion member; and installing a rod compression nut and a proximal expansion member coupled to the rod compression nut in the at least two rigid structures above the fixation rod, wherein bottom surfaces of the rod compression nut and the proximal expansion member are configured to bear against the fixation rod.

18. The method according to claim 17, further comprising removing a temporary screw cap from the at least two rigid structures, wherein the temporary screw cap is configured to be affixed at a proximal portion of the at least two rigid structures.

19. The method according to claim 18, further comprising removing middle portions of the at least two rigid structures, wherein the middle portions are configured to be disposed between the distal portions and the proximal portion of the at least two rigid structures, wherein each of the at least two rigid structures includes a breakaway portion separating the distal portion and the middle portion along which the middle portion is configured to be removed from the distal portion.

20. The method according to claim 17, wherein the tabs and the rigid structures are configured to be angularly disposed with respect to one another.

21. The assembly according to claim 20, wherein the tabs and the rigid structures are configured to be substantially perpendicular to each other.

22. The method according to claim 17, wherein each of the distal portions of the at least two rigid structures include a threaded portions; said installing the screw compression nut and the distal expansion member step further comprises steps of: using the screw compression nut, engaging the threaded portions of the at least two rigid structures; driving down the distal expansion member between the at least two rigid structures.

23. The method according to claim 22, wherein said installing the rod compression nut and the proximal expansion member step further comprises steps of: using the rod compression nut, engaging the threaded portions of the at least two rigid structures; and driving down the proximal expansion member between the at least two rigid structures; and securing the fixation rod between the combination of the rod compression nut and the proximal expansion member and the combination of the screw compression nut and the distal expansion member.

* * * * *